(12) United States Patent
Kolen et al.

(10) Patent No.: US 9,702,866 B2
(45) Date of Patent: Jul. 11, 2017

(54) GLATIRAMER ACETATE HUMAN MONOCYTIC CELL LINE-BASED POTENCY ASSAY

(71) Applicant: SYNTHON B.V., Nijmegen (NL)

(72) Inventors: Sebastianus Martinus Henricus Kolen, Nijmegen (NL); Francisca Antoinette Adriana Weijts, Nijmegen (NL)

(73) Assignee: SYNTHON B.V., Nijmegen (NL)

( * ) Notice: Subject to any disclaimer, the term of this patent is extended or adjusted under 35 U.S.C. 154(b) by 0 days.

(21) Appl. No.: 14/785,800

(22) PCT Filed: Apr. 25, 2014

(86) PCT No.: PCT/EP2014/058445
§ 371 (c)(1),
(2) Date: Oct. 20, 2015

(87) PCT Pub. No.: WO2014/174070
PCT Pub. Date: Oct. 30, 2014

(65) Prior Publication Data
US 2016/0091486 A1  Mar. 31, 2016

(30) Foreign Application Priority Data
Apr. 26, 2013  (WO) ............... PCT/EP2013/058787

(51) Int. Cl.
G01N 33/53    (2006.01)
G01N 33/50    (2006.01)
G01N 33/68    (2006.01)
G01N 33/567   (2006.01)

(52) U.S. Cl.
CPC ....... *G01N 33/5011* (2013.01); *G01N 33/505* (2013.01); *G01N 33/5023* (2013.01); *G01N 33/5047* (2013.01); *G01N 33/6863* (2013.01); *G01N 2333/57* (2013.01); *G01N 2333/7155* (2013.01); *G01N 2800/285* (2013.01)

(58) Field of Classification Search
None
See application file for complete search history.

(56) References Cited

U.S. PATENT DOCUMENTS 3,849,550 A    11/1974   Teitelbaum et al.

FOREIGN PATENT DOCUMENTS

| WO | WO 95/31990 A1 | 11/1995 |
| WO | WO 03/048735 A2 | 6/2003 |
| WO | WO 2008/157697 A2 | 12/2008 |

OTHER PUBLICATIONS

Carpintero et al, PNAS, 2010, vol. 107, No. 41, pp. 17692-17697.*
Burger, D., et al., "Glatiramer acetate increases IL-1 receptor antagonist but decreases T cell-induced IL-1β in human monocytes and multiple sclerosis," *PNAS* 106(11):4355-4359, National Academy of Sciences, United States (2009).
Farina, C., et al., "Immunological assay for assessing the efficacy of glatiramer acetate (Copaxone) in multiple sclerosis," *Journal of Neurology* 249(11): 1587-1592, Springer-Verlag, Germany(2002).
International Search Report and Written Opinion for International Application No. PCT/EP2014/058445, European Patent Office, The Netherlands, mailed on Jul. 17, 2014, 10 pages.

* cited by examiner

*Primary Examiner* — Bridget E Bunner
*Assistant Examiner* — Fozia Hamud
(74) *Attorney, Agent, or Firm* — Sterne Kessler Goldstein & Fox

(57) ABSTRACT

The present invention relates to a method to determine the potency of a batch of glatiramer acetate comprising stimulating human monocytic cell line cells with an effective amount of interferon (IFNγ), exposing the cells to a batch of glatiramer acetate, and determining the expression of the monocyte anti-inflammatory cytokine sIL-1Ra or the viability of the cells induced by glatiramer acetate.

16 Claims, 4 Drawing Sheets

GLATIRAMER ACETATE HUMAN MONOCYTIC CELL LINE-BASED POTENCY ASSAY

The present invention relates to a method to determine the potency of a batch of glatiramer acetate.

BACKGROUND OF THE INVENTION

Inflammation is a hallmark of multiple sclerosis (MS) which leads to demyelination and axonal loss resulting in neurodegeneration. Although it was sometimes claimed that neurodegeneration may be independent of inflammation, recent neuropathological studies provide clear evidence that whenever active tissue destruction is seen in MS, it occurs on the background of inflammation. It has been assumed for a long time that the pro-inflammatory cytokines tumor necrosis factor (TNF) and interleukin-1β (IL-1β) play an important part in MS progression and severity. To restrain inflammation in normal physiology, pro-inflammatory reactions are closely interconnected with counter-regulatory anti-inflammatory pathways. IL-1β activity is restrained by several molecules including the decoy IL-1 receptor II (IL-1RII) and its soluble form and the secreted form of IL-1 receptor antagonist (sIL-1Ra) which binds IL-1RI without triggering signaling. Both IL-1β and sIL-1Ra are mainly produced by monocytes/macrophages, which, together with T lymphocytes, are important parts of cellular infiltrate in the central nervous system (CNS) of MS patients.

Evidence of IL-1 system involvement in MS, although abundant, remains indirect. A combination of polymorphisms in the IL-1β (IL1B) and sIL-1Ra (IL-1RN) genes has been correlated with MS disease severity. Higher in vitro sIL-1Ra production has been observed in carriers of IL-1RN allele 2, with an indication of an allelic dose-effect relationship. In a study including 377 MS patients, significant associations between IL-1 genotypes and clinical outcome were found. The same trends were subsequently demonstrated in a second independent group of 67 primary progressive MS patients, suggesting that genetically determined immunomodulation mediated by IL-1 influences long-term prognosis in MS. Families displaying high IL-1β/sIL-1Ra production ratio are at increased risk to have a relative with relapse-onset MS than families with a low ratio. Furthermore, IL-1β is expressed throughout the CNS particularly in inflamed lesion, and caspase-1 that is required for the processing of pro-IL-1β into active IL-1β is expressed MS plaques. Direct evidence of IL-1 system involvement was demonstrated in the animal model for MS: Experimental Autoimmune Encephalomyelitis (EAE). Indeed, mice KO for both IL-1α and IL-1β display resistance to EAE induction and reduced disease severity whereas EAE was induced in IL-1Ra KO mice in the absence of pertussis toxin. Last but not least, treatment of EAE animals with recombinant sIL-1Ra reduced disease severity. More recently, because of the importance of IL-1β in the polarization of TH17 T cells, the inhibition of IL-1β together with that of IL-23 by a MEK/ERK inhibitor was shown to dampen EAE severity.

Monocytes/macrophages play an important part in the pathogenesis of MS. Although the composition of the inflammatory infiltrate in the CNS varies depending on the type, stage and activity of MS, monocytes/macrophages are thought to be key effectors responsible for tissue damage. They predominate in active MS lesions, and the presence of myelin degradation products inside macrophages is one of the most reliable markers of lesion activity, and pro-inflammatory mediators of activated monocytes/macrophages contribute to myelin injury. Although pro-inflammatory cytokines are involved in destructive mechanisms, they may also participate in repair, e.g., TNF promotes proliferation of oligodendrocyte progenitors and remyelination.

Glatiramer acetate (GA) is a copolymer used as an immunomodulatory treatment in relapsing-remitting multiple sclerosis (RRMS). Although in vitro studies demonstrated GA to affect multiple target cells, its mechanisms of action are poorly understood. It has previously been shown that GA induces the production of the secreted form of IL-1 receptor antagonist (sIL-1Ra) in human monocytes and, in turn, enhances sIL-1Ra circulating levels in MS patients. See D. Burger et al. in PNAS, 2009, Vol. 106, No. 11, pages 4355-4359). Thus, IFNβ and GA, both immunomodulators used with comparable efficiency in MS therapy, induce the production of the IL-1β inhibitor, sIL-1Ra, in monocytes in vitro and enhance sIL-1Ra circulating levels in vivo. The ability of circulating sIL-1Ra to cross the blood-brain barrier indicates that it may inhibit the pro-inflammatory activities of IL-10 into the CNS, a mechanism particularly important in regard to GA whose high polarity and hydrophilic nature is likely to impede CNS penetration. Therefore, sIL-1Ra might mediate part of the beneficial anti-inflammatory effects of GA at the periphery and into the CNS.

Glatiramer acetate (GA, COPAXONE®: 20 mg/ml GA) was FDA approved in 2002 for the treatment of relapsing forms of MS, including RRMS. GA is a copolymer and consists of the acetate salts of synthetic polypeptides made up of the naturally occurring amino acids glutamic acid, lysine, alanine, and tyrosine in specific molar ratios. To this end, see WO 95/31990 and U.S. Pat. No. 3,849,550 cited therein. Its activity or potency is conventionally tested in an experimental animal model, notably the experimental autoimmune encephalomyelitis (EAE) mouse model. Typically, the potency of a test batch of GA is compared with a reference batch of GA. These animal studies however are elaborate, expensive, and use large numbers of test animals, which experience significant discomfort levels, and there is therefore a need for a faster and cheaper potency test which does not require test animals.

WO 03/048735 describes a first improvement over the conventional EAE mouse in vivo model. It relates to an ex-vivo mouse lymph node cell-based potency test, determining the amount of the cytokine IL-2 secreted by said cells, but it still requires immunizing female mice with GA, sacrificing mice after immunization, and is directed to T cells instead of monocytic cells.

WO 2008/157697 discloses a method for testing an amino acid copolymer by simultaneously exposing cells to the copolymer in combination with a (proinflammatory) cytokine, and determining the expression of a protein induced by said cytokine. The amino acid copolymer can be glatiramer acetate. Examples of suitable cells include (myeloid) cells such as human acute monocytic leukemia cells (THP-1), human leukemic monocyte lymphoma cells (U937), and human promyelocytic leukemia cells (HL-60). Examples of suitable (proinflammatory) cytokines include tumor necrosis factor alpha (TNFα), interferon gamma (IFNγ), interleukin-1 beta (IL-1β), interleukin-6 (IL-6), and interleukin-8 (IL-8). Examples of proteins regulated by said cytokines include γ-interferon-inducible protein 10 (IP-10, CXCL10), interferon-inducible T cell α-chemoattractant (I-TAC, CXCL11), and monokine induced by γ-interferon (MIG, CXCL9).

Table 3 shows the GA (0-400 mg/ml) dose dependence of IFNγ (10 ng/ml) mediated induction of IP-10, I-TAC, and MIG in THP-1 cells and the description above said table (on page 23) mentions that the assay can be used to compare two or more copolymer preparations. However, the presented data cannot be fitted using a linear, or a non-linear four-parameter logistic model, as described in the USP chapter <1034> on analysis of biological assays, including cell based potency assays. These data are thus not suitable to quantitatively determine the potency of a GA test batch relative to a reference batch of GA (see the Examples below).

Furthermore, when repeating these experiments, the present inventors found that the glatiramer acetate concentration required to generate a chemokine response (i.e. 100 µg/ml, see FIG. 2 below), induces cell death in IFNγ-activated THP-1 cells (see FIG. 3 below).

Hence, there is a need for an improved cell-based potency assay for GA, which can be routinely used to quantitatively determine the relative potency of a batch of GA as compared to a reference batch of GA at GA concentrations that do not affect cell viability.

DETAILED DESCRIPTION OF THE PRESENT INVENTION

The present invention relates to a method to determine the potency of a batch of glatiramer acetate comprising stimulating human monocytic cell line cells with an effective amount of interferon gamma (IFNγ), exposing said cells to said batch of glatiramer acetate (GA), and determining the expression of the monocyte anti-inflammatory cytokine sIL-1Ra, i.e. the secreted form of IL-1 receptor antagonist, or the viability of said cells induced by glatiramer acetate.

In one embodiment of the present invention, the method further comprises determining the relative potency by comparing the potency of a batch of GA with the potency of a reference batch of GA.

An important advantage of the present invention method is that well-defined human monocytic cell line cells are used, which allows for reproducible test results. It further allows quantification of relative potency between batches. It is faster and cheaper, since it does not involve testing on animals, which is advocated by regulatory authorities, and it is clinically relevant since it determines the expression of an anti-inflammatory cytokine with known effect in MS.

In the context of the present invention, with glatiramer acetate (GA) is meant any synthetic polypeptide or copolymer made up of the amino acids tyrosine (Y), glutamic acid (E), alanine (A), and lysine (K) in all molar ratios as well as known variations thereof made up of the amino acids tyrosine (Y), phenylalanine (F), alanine (A), and lysine (K), and salts thereof, in particular acetate salts thereof. See the paragraph starting with "Glatiramer acetate" bridging pages 1 and 2 of WO 03/048735 and the definitions of "amino acid copolymer" on pages 6 and 7 of WO 2008/157697, as well as WO 95/31990 and U.S. Pat. No. 3,849,550 cited therein. Suitable examples of a batch of glatiramer acetate to be used in accordance with the present invention include COPAX-ONE® (20 mg/ml glatiramer acetate) and any and all generic versions thereof.

In the context of the present invention, with a monocyte anti-inflammatory cytokine is meant any signaling molecule that is produced by any cell of the monocytic lineage and exerts inhibitory (anti-inflammatory) effects on other cells of the immune system. In accordance with the present invention, said cytokine is the secreted form of IL-1 receptor antagonist (i.e. sIL-1Ra).

Particularly useful human monocytic cell line cells are human acute monocytic leukemia cells (THP-1) and human monocytic leukemia cells Mono Mac 6 (MM6). Human leukemic monocyte lymphoma cells (U937) were found to be not responsive to GA. In a preferred embodiment of the present invention, human acute monocytic leukemia cells (THP-1) are used.

Human monocytic cells are brought into a suitable medium, e.g. RPMI 1640 medium, typically supplemented with fetal bovine serum (FBS), and are stimulated with an effective amount of IFNγ, contacted with GA and the effect on the expression of the monocyte anti-inflammatory cytokine sIL-1Ra or the cell viability is measured.

Figure 3:
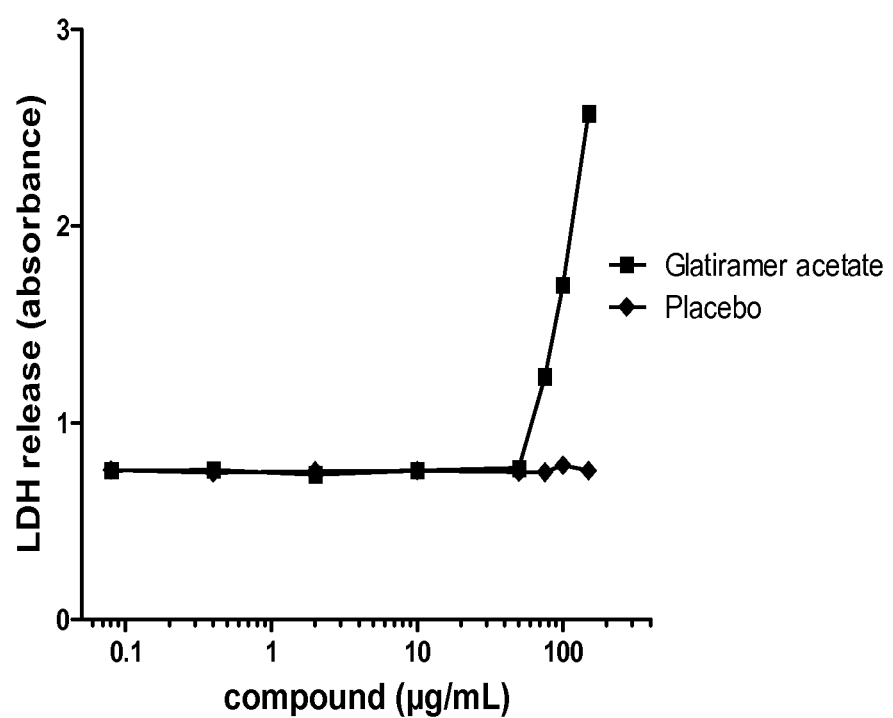
FIG. 3 shows glatiramer acetate-induced lactate dehydrogenase (LDH) release (as a marker for cell death) in IFNγ (10 ng/ml)-activated THP-1 cells at glatiramer acetate concentrations (i.e. 100 µg/ml) used in WO 2008/157697 to generate a chemokine response.

The present inventors surprisingly have found that excellent dose-response curves can be obtained when the expression of sIL-1Ra or cell viability is measured in human monocytic cell line cells that are stimulated with IFNγ when said cells are exposed to relatively low amounts of GA, typically in the range of 0.001-50 µg/ml, preferably in the range of 0.001-20 µg/ml. Above 50 µg/ml less meaningful results are obtained, because results may be confounded by the induction of cell death in the cell system at those conditions as shown in FIG. 3.

Typically, sIL-1Ra data are plotted against the log transformed glatiramer acetate concentration (in log µg/ml). Dose-response curves are generated by GA activation of monocytic cells and EC50 values are calculated using a non-linear parameter logistic model on semi-log transformed data, consistent with USP chapter <1034> on analysis of biological assays.

Instead of plotting sIL-1Ra data back-calculated using a calibration curve (in pg/ml), one may also plot absorbance ($OD_{450-570\ nm}$) against the log transformed glatiramer acetate concentration (in log µg/ml).

In accordance with the method of the present invention an effective amount of IFNγ should be used, and such amounts may be different for different human monocytic cell line cells and may also vary from batch to batch of IFNγ. Optimal effective concentration can for example determined based on a sIL-1Ra response curve quality. Said sIL-1Ra response curve quality may be generated with reference glatiramer material and different concentrations of the IFNγ batch to be tested.

The range using commercially available sources of IFNγ could vary between 0.05-100 ng/ml IFNγ.

In a typical embodiment of the present invention when determining the expression of sIL-1Ra, human monocytic cells, in particular THP-1 cells, are stimulated with a concentration in the range of 2-20 ng/ml.

In another embodiment of the present invention, the viability of human monocytic cell line cells, particularly THP-1 cells, is measured. Suitable methods to determine viability of human monocytic cell line cells are well-known to the person skilled in the art. One suitable method is measuring ATP levels (for instance the CellTiter-Glo® Luminescent Cell Viability Assay is a homogeneous method to determine the number of viable cells in culture based on quantitation of the ATP present, which signals the presence of metabolically active cells) after a suitable time period, typically after 96-144 hours, particularly after 120 hours. When determining the number of viable cells, similar or slightly higher concentrations of IFNγ can be used as described above.

The present invention also relates to a process for preparing a batch of glatiramer acetate (GA) which is acceptable for pharmaceutical use comprising a) preparing a batch of glatiramer acetate, b) measuring the relative potency of said batch according to the method described above, and c) qualifying the batch as acceptable for pharmaceutical use if the relative potency complies to the pre-defined specifications.

In one embodiment of the present invention, said pharmaceutical use is for the treatment of multiple sclerosis (MS), in particular relapsing forms of MS, including relapsing-remitting MS (RRMS).

The present invention is illustrated by the following examples.

EXAMPLES

Thawing of THP-1 Cells

Add 10 ml RPMI-1640 Medium (Lonza/Cambrex, #12-70F) with 10% FBS (fetal bovine serum) to a 15 ml sterile tube.
Remove one vial of THP-1 cells (ATCC, #TIB-202) from the liquid nitrogen storage tank and thaw the cells in the vial by gentle agitation in a 37° C.±1° C. water bath until almost totally thawed.
Sterilize the outside of the vial using a wipe, soaked in 70% (v/v) ethanol.
Using good aseptic technique, open the vial and transfer the contents of the vial into a Falcon tube, adding 10 ml of the pre-warmed RPMI-1640 plus 10% FBS.
Spin down at approximately 200 g for 5 minutes. Afterwards, discard the supernatant.
Resuspend the pellet into 10 ml pre-warmed RPMI-1640 plus 10% FBS, and transfer the cell suspension to a T-25 culture flask.
Place the T-25 cell culture flask into a humidified incubator at 37±1° C. and 5.0±1% $CO_2$.

Sub-Culturing (Passaging) of THP-1 Cells

THP-1 cells are sub-cultured every 3 or 4 days.
Collect cells and spin down at 200 g for 5 min. Resuspend the pellet in 10 ml with fresh pre-warmed RPMI-1640 plus 10% FBS.
Take a sample for cell counting.
Dilute the cells to a density of $2.0 \times 10^5$ cell viable cells/ml with fresh pre-warmed RPMI-1640 plus 10% FBS, and add 30 ml of the cell suspension to a new T-75 culture flask.
Place the T-75 culture flask into a humidified incubator at 37±1° C. and 5.0±1% $CO_2$.

Preparing and Storing IFNγ Stock Solutions

IFNγ ordered from R&D Systems (#285-IF) should be stored at −20° C. before reconstitution.
To reconstitute, add 0.5 ml sterile PBS to the IFNγ vial and gently swirl until the powder dissolves. The solution has a concentration of 0.2 mg/ml.
Aliquot the stock solution in 5×100 μl portions and store the vials at −80° C. until further use.
Thaw a vial containing a 0.2 mg/ml aliquot. Add 8910 μl sterile PBS to 90 μl 0.2 mg/ml IFNγ aliquot and pipette up and down. Aliquot in 25×200 μl portions and store the vials at −80° C. until further use.

Preparing IFNγ Working Solution

To make the IFNγ working solution at the day of the method run, thaw one IFNγ aliquot containing 200 μl with a concentration of 2 μg/ml.
For each plate, take 150 μl from the IFNγ aliquot and dilute the solution with 5850 μl RPMI-1640 plus 10% FBS to a concentration of 50 ng/ml. This is the IFNγ working solution and will result in a final concentration of 12.5 ng/ml in the assay.

Seeding of the Cell Plate

THP-1 cells are harvested and centrifugated at 200 g for 5 minutes.
Resuspend the pellet in 10 ml fresh pre-warmed RPMI-1640 plus 10% FBS. Take a sample for cell counting.
After cell count, adjust the cell density to $1.5 \times 10^6$ cells/ml and add 100 μl of the THP-1 cell suspension to the wells of a 96-wells plate.

Treating of the Cells

Prepare the glatiramer acetate dilution series. The stock concentration is 20 mg/ml, which needs to be diluted in RPMI-1640 plus 10% FBS to a working stock concentration of 80 μg/ml for the highest dilution. Make a dilution series in RPMI-1640 plus 10% FBS starting at a concentration of 80 μg/ml going down to 20 ng/ml.
Add 50 μl of the IFNγ working solution to the assay plate containing the cells. Add 50 μl of the glatiramer acetate dilutions to the plate containing the cells and the IFNγ working solution. The final dose-range of glatiramer acetate is between 20 and 0.005 μg/ml.
Incubate cells for 72 hours at 37° C. in an incubator with 5% $CO_2$, 93% humidity.

Supernatant Harvest and ELISA

After 72 hours of incubation centrifuge the 96-well plate at 200 g for 5 minutes.
Transfer 125 μl of the cell-free supernatant/well to a storage plate.
sIL-1Ra is determined in the cell supernatants using the sIL-1Ra ELISA kit from Quantikine, R&D, Minneapolis, Minn. (Cat # DRA00B) following the manufacturer's instructions. The remainder of the supernatant is stored in a closed storage plate at −80° C.

Data Analysis

Data on sIL-1Ra concentration are analyzed for relative potency as described in USP chapter <1034> section 3.4 on nonlinear models for quantitative responses. The software package GraphPad Prism (5.x) is used for fitting to a nonlinear model to the data:

sIL-1Ra data (in pg/ml) are plotted against the log transformed glatiramer acetate concentration (in log μg/ml).
A four-parameter logistic model is constructed to fit the dose response curves of the Reference (RS) and the test batch (TA). To test if the dose response curves for the Reference and test batch are parallel (i.e. dose response curves of Reference and test are identical in shape but differ only in a constant horizontal difference) a likelihood ratio test may be used comparing the following two models: 1) separate models fitted for the reference and test batch for top, bottom, slope and EC50, 2)

reduced model with common top, bottom and slope fitted to the Reference and test batch but with a different EC50. The four parameters in these fits are top and bottom asymptotes, slope, and EC50. A log likelihood ratio test is used to determine parallelism of results, since the reduced model (assuming parallelism) is contained in the full model (freely fitting both RS and TA curves).

Upon confirmation of parallelism the reduced model will be fitted and the EC50 for the Reference and test batch will be estimated by EC50RS and EC50TA respectively. The relative potency of the test batch will be estimated as:

Relative potency=EC50RS/EC50TA*100%

Cell Viability

The number of metabolically active cells in the cultures is determined by the CellTiter-Glo® Luminescent Cell Viability Assay (Promega, G7571). This is a homogeneous method of determining the number of viable cells in culture in multi-well plates. It is based on quantitation of adenosine tri-phosphate (ATP), which signals the presence of metabolically active cells.

Results Shown in FIGS. 1-4

Figure 1:
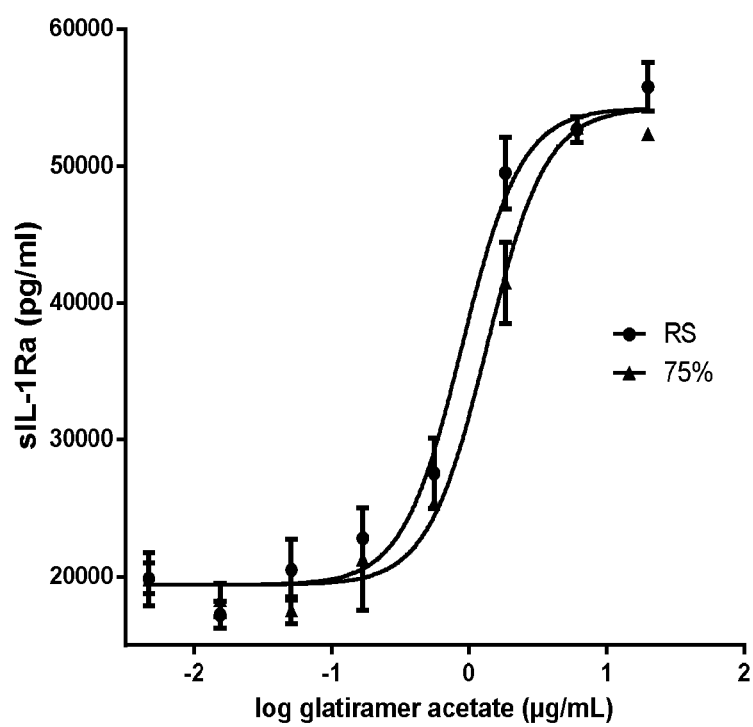
FIG. 1 shows sIL-1Ra expression of THP-1 cells after exposure to GA. Dose-response data were fit to a four-parameter logistic model to generate curves.

FIG. 1 shows sIL-1Ra expression of THP-1 cells after exposure to GA (Copaxone batch P53767). Cells were activated in medium containing 12.5 ng/ml IFNγ. The protocol was executed as described above. Results from the Copaxone (RS) batch and a TA batch mimicking a 75% potency sample are shown. Parallelism of results was established as described above. Calculated relative potency for the 75% nominal relative potency sample based on the determination of EC50 ratios was 66%. Goodness of fit ($R^2$) is 0.98.

Figure 2:
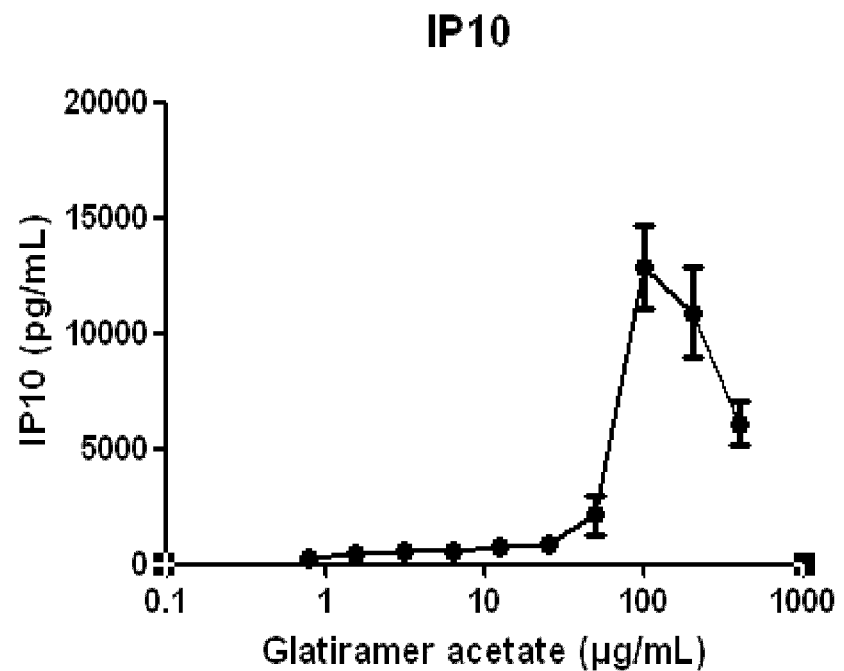
FIG. 2 depicts the dose-response curve as derived from the data on IP-10 shown in Table 3 of WO 2008/157697 in IFNγ (10 ng/ml)-activated THP-1 cells.

In FIG. 2, the dose-response curve as derived from the data on IP-10 shown in Table 3 of WO 2008/157697 is depicted. As can be seen, this curve has a very steep slope, only a single point in the sloping part of the curve, and a pronounced hook effect at high dosages. From this dose-response curve it cannot be demonstrated that a THP-1 cell-based assay with IP-10 as response is suitable for potency calculations. Similar results were obtained for the I-TAC and MIG data in Table 3.

Furthermore, FIG. 3 shows that the glatiramer acetate concentration required to generate a chemokine response (i.e. 100 μg/ml, see FIG. 3), induces cell death in IFNγ-activated THP-1 cells.

Figure 4:
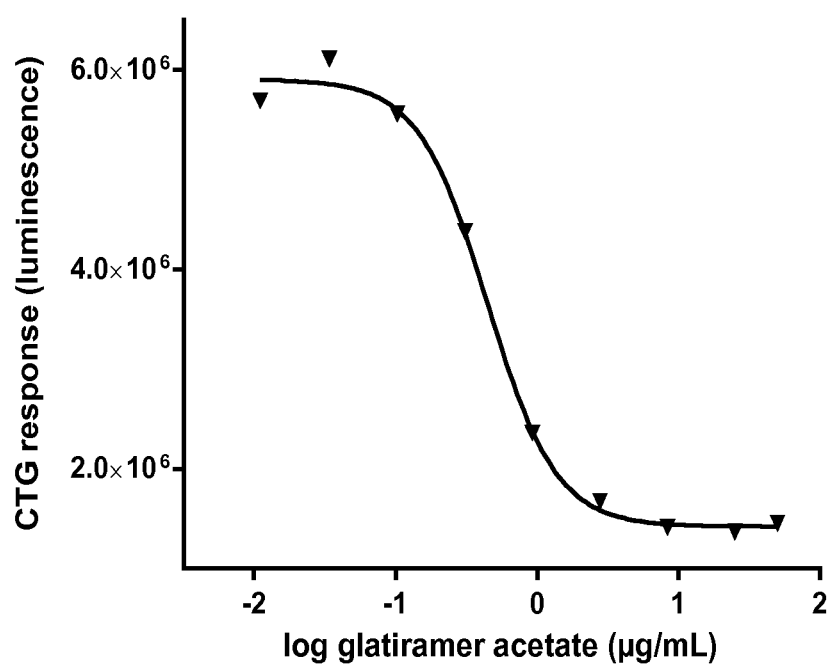
FIG. 4 shows cell viability by glatiramer acetate in IFNγ (25 ng/ml)-activated THP-1 cells as determined after 120 h of culture by measurement of ATP levels.

FIG. 4 shows cell viability inhibition by glatiramer acetate in IFNγ (25 ng/ml)-activated THP-1 cells as determined after 120 h of culture by measurement of ATP levels.

The above data show that human monocytic cell lines can be used to assess the activity or potency of GA after stimulation of said cells by IFNγ. The parallellism of the four-parameter sigmoid dose-response curves in FIG. 1 indicate that the assay with sIL-1Ra as response is suitable to calculate the relative potency of batches against a reference batch.

In the presence of IFNγ, GA induces sIL-1Ra secretion from THP-1 cells, which is paralleled by a simultaneous decrease in cell viability (as measured by ATP activity). Both read-outs (sIL-1Ra and ATP levels) result in S-shaped dose-response curves that can be fitted by a four-parameter logistic model and both are suitable to quantify relative potency. Both response parameters are very sensitive to GA and full response curves can be obtained at concentrations that do not affect cell death.

The invention claimed is:

1. A method to determine the relative potency of a batch of glatiramer acetate (GA) comprising stimulating human monocytic cell line cells with an effective amount of interferon gamma (IFNγ), contacting said cells with a dose of GA, determining the expression of the monocyte anti-inflammatory cytokine, secreted form of IL-1 receptor antagonist (sIL-1 Ra), and determining said relative potency by comparing a batch of GA with a reference batch of GA, and wherein parallel dose response curves for said expression of the monocyte anti-inflammatory cytokine sIL-1Ra, for the batch of GA and the reference batch of GA, determines the relative potency of said batch of GA compared with the potency of said reference batch of GA.

2. The method according to claim 1, wherein said GA is a copolymer consisting of the acetate salts of synthetic polypeptides made up of the amino acids tyrosine, glutamic acid, alanine, and lysine in all molar ratios.

3. The method according to claim 1, wherein said human monocytic cell line cells are selected from human acute monocytic leukemia cells (THP-1) and human monocytic leukemia cells Mono Mac 6 (MM6).

4. The method according to claim 3, wherein said cells are THP-1 cells.

5. The method according to claim 1, wherein the human monocytic cell line cells are contacted with 0.001-50 μg/ml GA.

6. The method according to claim 5, wherein the human monocytic cell line cells are contacted with 0.001-20 μg/ml GA.

7. The method according to claim 1, wherein said human monocytic cells are stimulated with a concentration of IFNγ determined based on sIL-1Ra response.

8. The method according to claim 7, wherein the concentration of IFNγ is 0.05-100 ng/ml.

9. The method according to claim 8, wherein the concentration of IFNγ is 2-20 ng/ml.

10. The method according to claim 8, wherein the concentration of IFNγ is 25 ng/ml.

11. The method according to claim 9, wherein the concentration of IFNγ is 12.5 ng/ml.

12. The method according to claim 1, wherein the human monocytic cell line cells are in RPMI 1640 medium supplemented with fetal bovine serum (FBS).

13. A method to determine the relative potency of a batch of GA comprising stimulating human monocytic cell line cells with 12.5 ng/ml of IFNγ, contacting said cells with 0.001-50 μg/ml of said batch of GA, determining the viability of said cells induced by GA by measuring (adenosine tri-phosphate) ATP levels and determining said relative potency by comparing a batch of GA with a reference batch of GA, and wherein parallel dose response curves for said ATP levels plotted against the log transformed GA concentration (μg/ml), for the batch of GA and the reference batch of GA, determines the relative potency of said batch of GA compared with the potency of said reference batch of GA.

14. The method according to claim 13, wherein said ATP levels are determined after 120 hours of culture.

15. A process for preparing a batch of GA for pharmaceutical use comprising,
a) preparing a batch of GA,
b) measuring the relative potency of said batch compared to a reference batch of GA, comprising, i) stimulating human monocytic cell line cells with 0.05-100 ng/ml of IFNγ,
ii) contacting said cells with 0.001-50 μg/ml of said batch of GA, and
   (a) determining the expression of the monocyte anti-inflammatory cytokine sIL-1Ra, or
   (b) determining the viability of said cells induced by GA, and
c) wherein parallel dose response curves for said expression of the monocyte anti-inflammatory cytokine sIL-1Ra or ATP levels, for the batch of GA and the reference batch of GA indicate that the batch is acceptable for pharmaceutical use.

16. The process of claim 15, wherein said pharmaceutical use is for the treatment of multiple sclerosis.

* * * * *